(12) United States Patent
Bhagat et al.

(10) Patent No.: US 11,059,042 B2
(45) Date of Patent: Jul. 13, 2021

(54) SYSTEMS AND METHODS FOR ENRICHING TARGET CELLS IN A SAMPLE

(71) Applicant: CLEARBRIDGE BIOMEDICS PTE LTD, Singapore (SG)

(72) Inventors: Ali Asgar S. Bhagat, Singapore (SG); Andrew En-Tzu Wu, Singapore (SG); Junquan Huang, Singapore (SG); Guofeng Guan, Singapore (SG); Shuzhe Chao, Singapore (SG); Yau Luong Koh, Singapore (SG); Yifang Lee, Singapore (SG); Man Chun Leong, Singapore (SG)

(73) Assignee: BIOLIDICS LIMITED, Singapore (SG)

( * ) Notice: Subject to any disclaimer, the term of this patent is extended or adjusted under 35 U.S.C. 154(b) by 0 days.

(21) Appl. No.: 16/098,025

(22) PCT Filed: May 4, 2016

(86) PCT No.: PCT/SG2016/050205
§ 371 (c)(1),
(2) Date: Oct. 31, 2018

(87) PCT Pub. No.: WO2017/192098
PCT Pub. Date: Nov. 9, 2017

(65) Prior Publication Data
US 2019/0151847 A1 May 23, 2019

(51) Int. Cl.
| | | |
|---|---|---|
| *C12M 1/00* | (2006.01) | |
| *B01L 3/00* | (2006.01) | |
| *G01N 1/00* | (2006.01) | |
| *G01N 1/40* | (2006.01) | |
| *G01N 33/574* | (2006.01) | |
| *G01N 15/10* | (2006.01) | |

(52) U.S. Cl.
CPC ... *B01L 3/502761* (2013.01); *B01L 3/502738* (2013.01); *B01L 3/502753* (2013.01); *C12M 47/04* (2013.01); *G01N 1/00* (2013.01); *G01N 1/40* (2013.01); *G01N 33/574* (2013.01); *B01L 2200/0605* (2013.01); *B01L 2200/0652* (2013.01); *B01L 2200/143* (2013.01); *B01L 2300/088* (2013.01); *B01L 2300/0864* (2013.01); *B01L 2400/0622* (2013.01); *G01N 2001/4083* (2013.01); *G01N 2015/1006* (2013.01)

(58) Field of Classification Search
None
See application file for complete search history.

(56) References Cited

U.S. PATENT DOCUMENTS

| | | |
|---|---|---|
| 2011/0207621 A1 | 8/2011 | Montagu et al. |
| 2015/0177122 A1 | 6/2015 | Foster et al. |
| 2015/0226657 A1 | 8/2015 | Foster et al. |
| 2019/0151847 A1* | 5/2019 | Bhagat ............... G01N 1/00 |

FOREIGN PATENT DOCUMENTS

| | | |
|---|---|---|
| CN | 101743303 | 6/2010 |
| EP | 0901578 | 3/1999 |
| EP | 1593968 | 9/2005 |
| EP | 2191895 | 10/2012 |
| EP | 2902108 | 8/2015 |
| JP | 2010-226978 | 10/2010 |
| JP | 2015-524674 | 8/2015 |
| WO | WO9745644 | 12/1997 |
| WO | WO2007084392 | 7/2007 |
| WO | WO 2008/13087 | 10/2008 |
| WO | WO2010106434 | 9/2010 |

(Continued)

OTHER PUBLICATIONS

Supplementary European Search Report and Search Opinion issued by the European Patent Office for European Application No. 16901116.0, dated Nov. 20, 2019, pp. 1-11.
First Office Action issued in the corresponding Japan Patent Application No. 2018-557005 dated Mar. 3, 2020.
International Search Report for International Patent Application No. PCT/SG2016/050205 dated Aug. 9, 2016.

(Continued)

*Primary Examiner* — Michael D Burkhart
(74) *Attorney, Agent, or Firm* — McDonnell Boehnen Hulbert & Berghoff LLP (57) ABSTRACT

A system for enriching target cells in a sample is disclosed. The system comprises a microfluidic chip comprising a sample inlet, a sample outlet, a waste outlet and a microfluidic channel, the sample inlet being coupled to an upstream end of the microfluidic channel and the sample outlet and the waste outlet being coupled to a downstream end of the microfluidic channel, the microfluidic chip being configured such that target cells are directed to the sample outlet and non-target cells are directed to the waste outlet; a sample input pump configured to introduce the sample into the sample inlet of the microfluidic chip; an output flow rate detector configured to measure a flow rate at the sample outlet and/or the waste outlet of the microfluidic chip; a sample collection switching valve having a configuration switchable between a first configuration in which the sample output of the microfluidic chip is coupled to a sample output container and a second configuration in which the sample output of the microfluidic chip is coupled to a waste output container; and a controller configured to control the configuration of the sample collection switching valve using the flow rate measured by the output flow rate detector.

20 Claims, 6 Drawing Sheets

(56) References Cited

FOREIGN PATENT DOCUMENTS

| WO | WO2011090396 | 7/2011 |
| WO | WO2012142664 | 10/2012 |
| WO | WO2014193304 | 12/2014 |
| WO | WO 2015/002975 | 1/2015 |
| WO | WO 2015002975 | 1/2015 |
| WO | WO2015057159 | 4/2015 |
| WO | WO2015057166 | 4/2015 |
| WO | WO2015200857 | 12/2015 |
| WO | WO 2016010861 | 1/2016 |

OTHER PUBLICATIONS

International Preliminary Report on Patentability for International Patent Application No. PCT/SG2016/050205 dated Apr. 3, 2018.
Written Opinion of the International Searching Authority for International Patent Application No. PCT/SG2016/050205 dated Aug. 9, 2016.
Office Action for European Patent Application No. 16901116.0 dated Oct. 13, 2020.
Office Action for Japan Patent Application No. 2018-557005 dated Nov. 6, 2020 (English translation attached).
Sheilds et al., "Microfluidic Cell Sorting: A Review of the Advances in the Separation of Cells from Debulking to Rare Cell Isolation" Lab Chip 15(5):1230-1249 (Feb. 2015).
English Translation of Office Action from Chinese counterpart application CN 201680085349.7; dated Mar. 16, 2021, pp. 1-16.

* cited by examiner

SYSTEMS AND METHODS FOR ENRICHING TARGET CELLS IN A SAMPLE

This application is a U.S. National Phase application under 35 U.S.C. § 371 of PCT/SG2016/050205, filed May 4, 2016, the specification of which is hereby incorporated by reference in its entirety.

FIELD OF THE INVENTION

Embodiments of the present invention relate to the fields of oncology and diagnostic testing. More specifically, embodiments of the present invention relate to systems and methods for enrichment and identification of target cells from a sample.

BACKGROUND

Cancer cells disseminate from primary tumour through blood as circulating tumour cells (CTC), and invade distant sites to form metastatic lesions. Other means of cancer cell dissemination or accumulation in other medium include pleural effusions, peritoneal fluid, urine or combinations thereof. As high as 90% of all cancer related deaths are attributed to metastasis, the spread of cancer to distant sites. Circulating malignant tumour cells provide information on the metastatic aggressiveness and molecular insights into the primary tumour or foreboding metastatic lesion. These malignant cells are present at extremely low frequencies; about 1-10 CTC can be found in a billion ($10^9$) blood cells. Their rarity, coupled with highly heterogeneous nature, has thus far limited the use of CTCs for clinical monitoring and cancer management.

One method of enriching CTCs is to use bio chip designs based on inertial microfluidic technologies involving sorting/enrichment of target cells in a cell suspension buffer based on their physical or mechanical properties. These technologies are able to deplete the untargeted components of the samples, which are mostly considered as contaminations for the successful identification of malignant tumour cells using various downstream analysis techniques.

The performance of microfluidic based biochips can be easily influenced by external factors such as pulsation in the pumping module, bubbles, and pressure changes. In the case of an enrichment platform, changes in the pressure and resistances can impact the quality of enrichment.

SUMMARY OF THE INVENTION

According to a first aspect of the present invention there is provided a system for enriching target cells in a sample. The system comprises a microfluidic chip comprising a sample inlet, a sample outlet, a waste outlet and a microfluidic channel, the sample inlet being coupled to an upstream end of the microfluidic channel and the sample outlet and the waste outlet being coupled to a downstream end of the microfluidic channel, the microfluidic chip being configured such that target cells are directed to the sample outlet and non-target cells are directed to the waste outlet; a sample input pump configured to introduce the sample into the sample inlet of the microfluidic chip; an output flow rate detector configured to measure a flow rate at the sample outlet and/or the waste outlet of the microfluidic chip; a sample collection switching valve having a configuration switchable between a first configuration in which the sample output of the microfluidic chip is coupled to a sample output container and a second configuration in which the sample output of the microfluidic chip is coupled to a waste output container; and a controller configured to control the configuration of the sample collection switching valve using the flow rate measured by the output flow rate detector.

The flow rate ratio between the target cells output and the waste output for a two output biochip, for example, can be used as a parameter to assess the quality of enrichment. If this ratio is lower than the set value, then the recovery of the target cells (malignant tumour cells) may decrease as more cells are lost to the waste. On the contrary, if the said ratio is higher than the set value, there will be more contaminating non-target cells that would be collected with the target cells thus decreasing enrichment. This ratio may vary considerably during manual manipulation as the output tubing resistance, and open pressure may not be well controlled.

In an embodiment the controller is configured to compare the flow rate measured by the output flow rate detector with a predetermined range of flow rate values, and the controller is further configured to switch the sample collection switching valve to the second configuration if the flow rate measured by the output flow rate detector is outside the predetermined range of flow rate values.

The predetermined range of flow rates is may be range within 10% or 5% of a predetermined flow rate.

In an embodiment the controller is configured to determine a flow ratio between the sample outlet and the waste outlet and further configured to compare the flow ratio with a predetermined range of flow ratios and to switch the sample collection switching valve to the second configuration if the flow ratio is outside the predetermined range of flow ratios.

In an embodiment the controller is configured to determine the flow ratio from the flow rate measured by the output flow rate detector and a total flow rate through the microfluidic chip.

In an embodiment the system comprises a first output flow rate detector configured to measure a flow rate at the sample outlet and a second output flow rate detector configured to measure a flow rate at the waste outlet of the microfluidic chip, wherein the controller is configured to determine the flow ratio from a first flow rate measured by the first flow rate detector and a second flow rate measured by the second flow rate detector.

In an embodiment the sample comprises a density matching liquid having a density selected such that the target cells are uniformly suspended in the sample.

In an embodiment the microfluidic chip further comprises a diluent inlet coupled to the upstream end of the microfluidic channel and the system further comprise a diluent inlet pump configured to introduce a diluent buffer into the diluent inlet.

The diluent buffer may comprise an isotonic solution; and/or a surfactant solution. An isotonic solution in the diluent buffer may assist in maintaining high cell integrity during processing. A surfactant solution may reduce the shear forces experienced by cells and therefore maintain cell viability.

In an embodiment the system further comprises a debubbler arranged to remove bubbles from the diluent buffer.

The sample may comprise a blood sample. The target cells may be circulating tumour cells.

In an embodiment, the microfluidic channel comprises a spiral or curved section.

According to a second aspect of the present invention there is provided a method of enriching target cells in a sample, using a microfluidic chip. The microfluidic chip comprises a sample inlet, a sample outlet, a waste outlet and a microfluidic channel, the sample inlet being coupled to an upstream end of the microfluidic channel and the sample outlet and the waste outlet being coupled to a downstream end of the microfluidic channel, the microfluidic chip being configured such that target cells are directed to the sample outlet and non-target cells are directed to the waste outlet. The method comprises: introducing the sample into the sample inlet of the microfluidic chip; monitoring a flow rate at the sample outlet and/or the waste outlet of the microfluidic chip; controlling the configuration of a sample collection valve using the monitored flow rate, the sample collection switching valve having a configuration switchable between a first configuration in which the sample output of the microfluidic chip is coupled to a sample output container and a second configuration in which the sample output of the microfluidic chip is coupled to a waste output container.

In an embodiment the method further comprises suspending the sample in a density matching liquid prior to introducing the sample into the sample inlet of the microfluidic chip, the density matching liquid having a density selected such that the target cells are uniformly suspended in the sample.

In an embodiment the method further comprises performing centrifugation and or blood lysis on the sample before introducing the sample into the sample inlet of the microfluidic chip.

In an embodiment the method further comprises comparing the monitored flow rate with a predetermined range of flow rate values, and switching the sample collection switching valve to the second configuration if the flow rate measured by the output flow rate detector is outside the predetermined range of flow rate values.

The predetermined range of flow rates is may be range within 10% or 5% of a predetermined flow rate.

In an embodiment the method further comprises determining a flow ratio between the sample outlet and the waste outlet, comparing the flow ratio with a predetermined range of flow ratios and to switching the sample collection switching valve to the second configuration if the flow ratio is outside the predetermined range of flow ratios.

In an embodiment determining the flow ratio comprises determining the flow ratio from the flow rate the sample outlet or the waste outlet of the microfluidic chip and a total flow rate through the microfluidic chip.

In an embodiment the method comprises measuring a first flow rate at the sample outlet and a measuring a second flow rate at the waste outlet of the microfluidic chip, wherein determining the flow ratio comprises determining the flow ratio from the first flow rate and the second flow rate.

In an embodiment the microfluidic chip further comprises a diluent inlet coupled to the upstream end of the microfluidic channel and the method further comprises introducing a diluent buffer into the diluent inlet.

The diluent buffer may comprise an isotonic solution; and/or a surfactant solution. An isotonic solution in the diluent buffer may assist in maintaining high cell integrity during processing. A surfactant solution may reduce the shear forces experienced by cells and therefore maintain cell viability.

In an embodiment the method further comprises removing bubbles from the diluent buffer before introducing the diluent buffer into the diluent inlet.

The sample may comprise a blood sample. The target cells may be circulating tumour cells.

In an embodiment, the microfluidic channel comprises a spiral or curved section.

According to an embodiment of the present invention a method of analysing a sample comprises enriching target cells in the sample using a method described above; and analysing the enriched target cells.

The analysis of the target cells may comprise detection of intra-cellular and/or extra-cellular protein markers; analysis of cell and nuclear morphology; and/or molecular characterization by sequencing of nucleic acids by next-generation sequencing (NGS) and/or Sanger sequencing, and/or digital polymerase chain reaction (PCR), and/or droplet digital PCR, quantitative PCR (qPCR) and/or fluorescence in-situ hybridization (FISH); and/or copy number variation of nucleic acids of interest.

BRIEF DESCRIPTION OF THE DRAWINGS

In the following, embodiments of the present invention will be described as non-limiting examples with reference to the accompanying drawings in which.

DETAILED DESCRIPTION

Embodiments of the present invention relate to methods for the enrichment of malignant tumour cells that allow for their downstream identification and characterisation from biological fluids from cancer patients.

Figure 1:
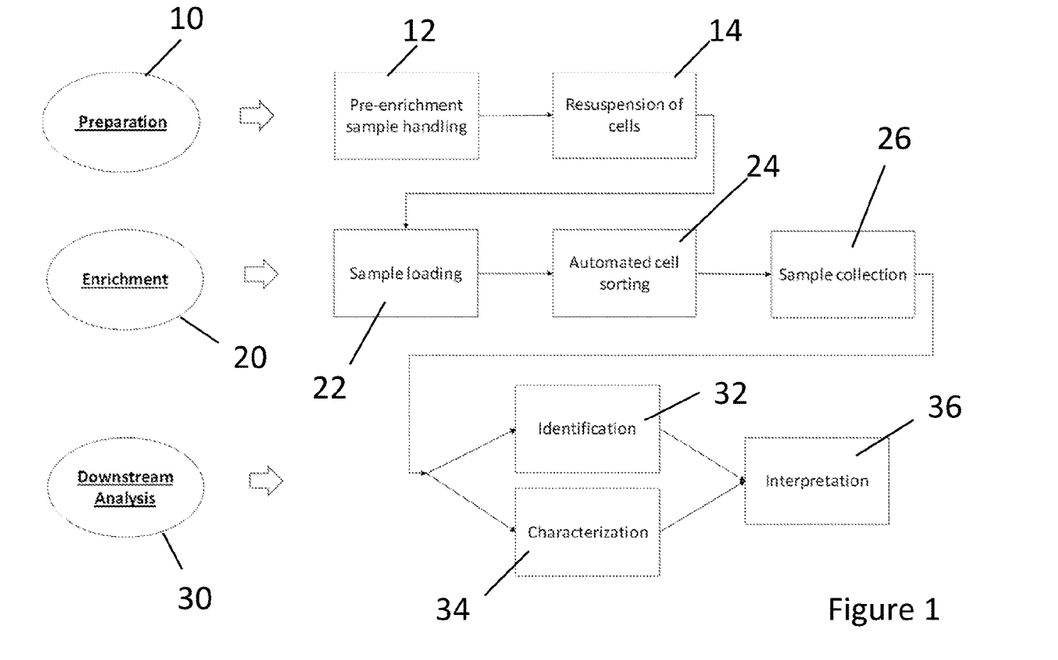
FIG. 1 is a flowchart showing a method of non-invasive identification and analysis of malignant tumour cells.

FIG. 1 is a flowchart showing a method of non-invasive identification and analysis of malignant tumour cells. As shown in FIG. 1, the method comprises three phases: preparation 10; enrichment 20; and downstream analysis 30.

In an embodiment the method of cancer cell enrichment 20, based on an inertial focusing principle coupled with Dean flow dynamics, requires a uniform suspension of cells that is subsequently processed by an automated system to stream malignant tumour cells and other cells into different collection tubes. Downstream visual or molecular analysis 30 of the cellular output can be performed to identify tumour characteristics that indicate the cell is indeed of a tumorigenic nature and provides molecular information relevant to cancer research or diagnostic use. The enrichment platform can be treated as a sample preparation method that allows the various downstream characterization techniques to be applied for analysis and to gather more information on cancer.

Figure 2:
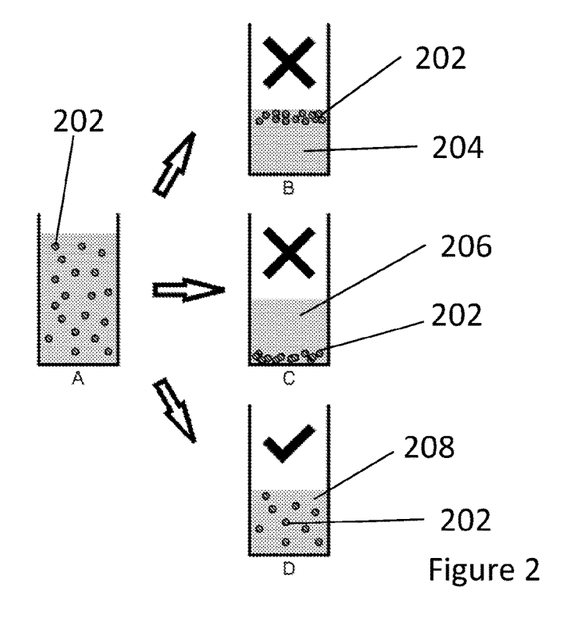
FIGS. 2A to 2D shows sample suspension in a preparation phase.

As shown in FIG. 1, the preparation phase 10 comprises pre-enrichment sample handling 12 and re-suspension of the cells 14. The input cell sample may be pre-enriched or pre-filtered to deplete certain components to boost the processing throughput and higher quality target cells enrichment. For example, centrifugation or red blood lysis may be performed to remove red blood cells in human peripheral blood sample to decrease total cellular load and reduce processing time. A cell strainer may be used to remove certain clots/tissue debris that may clog the tubing or channel, or disturb the flow stream inside the chip. The sample should then be suspended in certain volume of input buffer. The input buffer should consist of a density matching liquid to ensure that the cells do not sediment or are loss during processing. For example, if longer processing time is required, the density of the input buffer should then be adjusted close to the density of the cells to prevent the cells from flowing to the top layer of the buffer or sediment down to the bottom of the container during the processing, as shown in FIG. 2.

In embodiments for CTC enrichment from whole blood, the following reagents may be used in the preparation phase 10. A RBC lysis buffer or density-separation fluid may be used. The whole blood sample may be hemolysed using a ammonium chloride based red blood cell (RBC) lysis buffer or processed with density gradient centrifugation to separate out the nucleated cell fraction, including CTCs.

The enrichment phase 20 comprises sample loading 22 in which the sample is loaded onto a biochip for sorting; automated cell sorting 24 in which the cells of the sample are sorted, for example by using inertial forces to separate the cells according to cell size; and sample collection 26 in which the target cells of the sample are collected and non-target cells are discarded as waste.

The downstream analysis phase 30 comprises identification 32 and characterisation 34 of the isolated target cells and then interpretation 36 of the results of the identification and characterisation.

FIGS. 2A to 2D shows sample suspension in the preparation phase. As shown in FIG. 2A all the cells 202 are suspended uniformly when the sample is ready to process. The sample is then resuspended in a certain volume of input buffer. The density of the input buffer is controlled with a density matching liquid.

If as shown in FIG. 2B, the density of the cells 202 is lower than that of the surrounding buffer 204 so that the cells 202 will float up due to buoyancy force during the processing, uniformity of the suspension density is lost. If as shown in FIG. 2C the density of the cells 202 is higher than that of the surrounding buffer 206 so that the cells will sediment during the processing, uniformity of the suspension density is lost.

FIG. 2D shows a sample with the density of the buffer matched to the cells. As shown in FIG. 2D, the cells 202 are suspended uniformly using density matched buffer 208 during the entire processing stage.

As described above the input cell sample buffer is used to suspend the input cell sample to ensure minimal cell loss due to sedimentation effects. The input cell sample buffer consists of a density and viscosity matched solution that keeps the input cells neutrally buoyant allowing them to be processed for a long period of time.

Figure 3:
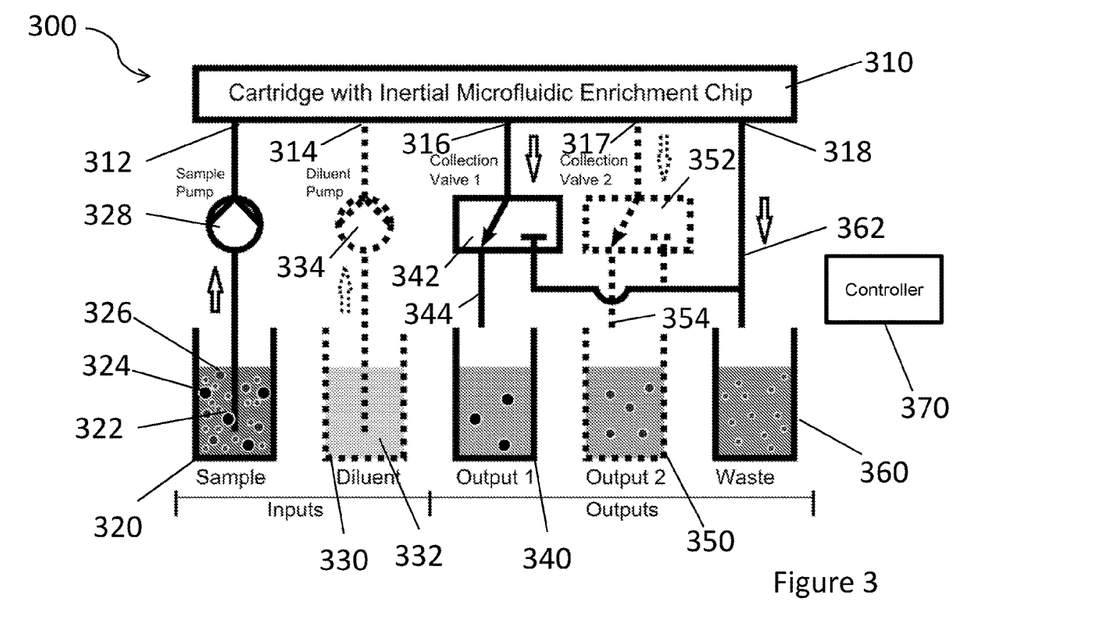
FIG. 3 is a schematic illustration of a system for enriching target cells according to an embodiment of the present invention.

FIG. 3 is a schematic illustration of a system for enriching target cells according to an embodiment of the present invention. The system 300 comprises a microfluidic chip 310. The microfluidic chip 310 is contained within a cartridge and comprises at least one microfluidic channel for separating cells according to their size using inertial forces. The microfluidic chip 310 can enrich target malignant tumour cells based on size and morphology of the cells with the help of the inertial forces and dean flows (Dean cycles). An example of a microfluidic chip is described in more detail below with reference to FIG. 4.

The system 300 further comprises a sample container 320 which contains a sample 322. The sample 322 comprises target cells suspended in an input buffer. In the embodiment shown in FIG. 3, the sample 322 comprises two types of target cells: first target cells 324 and second target cells 326. A sample pump module 328 is configured to feed the sample 322 into a sample inlet 312 of the microfluidic chip 310 from the sample container 320 with a constant flow rate.

The input cell sample 322 may be pre-enriched or pre-filtered to deplete certain components to boost the processing throughput and higher quality target cells enrichment. For example, centrifugation or red blood lysis may be performed to remove red blood cells in human peripheral blood sample to decrease total cellular load and reduce processing time. A cell strainer may be used to remove certain clots/tissue debris that may clog the tubing or channel, or disturb the flow stream inside the chip. The sample should then be suspended in certain volume of input buffer. The input buffer should consist of a density matching liquid to ensure that the cells do not sediment or are loss during processing. For example, if longer processing time is required, the density of the input buffer should then be adjusted close to the density of the cells to prevent the cells from flowing to the top layer of the buffer or sediment down to the bottom of the container during the processing, as described above with reference to FIG. 2.

The system 300 further comprises a diluent buffer container 330 which contains a diluent buffer fluid 332. A diluent buffer pump module 334 is configured to feed the diluent buffer fluid 332 into a diluent buffer inlet 314 of the microfluidic chip 310 from the diluent buffer container 330 with a constant flow rate.

In the embodiment shown in FIG. 3, the microfluidic chip 310 has three outputs: a first sample outlet 316; a second sample outlet 317 and a waste outlet 318. The system 300 further comprises three output containers: a first sample output container 340; a second sample output container 350 and a waste output container 360. The first sample outlet 316 of the microfluidic chip 310 is coupled to a first collection valve 342. The first collection valve 342 is configured to control whether the output from the first sample outlet is connected to a first sample output branch 344 coupled to the first sample output container 340 or a waste output branch 362 coupled to the waste output container 360. The second sample outlet 317 of the microfluidic chip 310 is coupled to a second collection valve 352. The second collection valve 352 is configured to control whether the output from the second sample outlet 317 is coupled to a second sample output branch 354 coupled to the second sample output container 350 or the waste output branch 362 coupled to the waste output container 360. The waste outlet 318 of the microfluidic chip 310 is coupled to the waste output branch 362.

A controller 370 is configured to monitor a first ratio and a second ratio. The first ratio is the ratio of the flow rate from the first sample outlet 316 to the flow rate from the waste outlet 318. The second ratio is the ratio of the flow rate from the second sample outlet 317 to the flow rate from the waste outlet 318. The controller 370 is configured to control the first collection valve 342 using the first ratio according to a first rule. The first rule may be as follows: if the first ratio is within a first range of values, direct the flow from the first sample outlet 316 to the first sample output container 340 via the first sample output branch 344 and if the first ratio is outside the first range of values, direct the flow from the first sample outlet 316 to the waste output container 360 via the waste output branch 362. The controller 370 is configured to control the second collection valve 352 using the second ratio according to a second rule. The second rule may be as follows: if the second ratio is within a second range of values, direct the flow from the second sample outlet 317 to the second sample output container 350 via the second sample output branch 354 and if the second ratio is outside the second range of values, direct the flow from the second sample outlet 317 to the waste output container 360 via the waste output branch 362.

The operation of the system 300 is as follows. Once the sample is prepared, the sample pumping module 328 to feeds the cell suspension sample to the microfluidic chip 310. If any diluent buffer fluid 330 is required, the diluent buffer pump module 324 feeds the diluent buffer liquid at a predetermined flow rate and the flow rate inside the microfluidic chip is allowed to equilibrate.

The controller 370 controls the input flow rates. As discussed above, the controller 370 also controls the first sample collection valve 342 and the second sample collection valve 352 according to rules. The rules are based on the ratio of the first sample outlet flow to the waste outlet flow and the ratio of the second sample outlet flow to the waste outlet flow. If one of these ratios is outside a range set by the rules, the controller 370 causes the first sample collection valve 342 or the second sample collection valve 352 to switch the flow from the first sample outlet 316 and/or the second sample outlet 317 to the waste output branch 362. When the flow ratio is outside the range set by the rules, this indicates that there is an abnormality which may be caused by debris or a bubble in the microfluidic chip 310. Such an abnormality will interfere with the separation of target cells by the microfluidic chip 310 and therefore output is switched to the waste output container 360 while the flow ratio is abnormal. The flow ratio can be fixed by controlling the resistances of the sample output and waste output branch (ensuring equal pressure drop across these branches). The resistances can be set by designing them into the microfluidic chip by designing the dimensions of the sample and waste outlet coupling paths (FIGS. 4 124 and 128) as well as the tubing in the system at the sample and waste output branches.

In the embodiment shown in FIG. 3, the microfluidic chip 310 has one sample inlet 312, one diluent buffer inlet 314, two sample outlets 316 317 and one waste outlet 318. It is to be understood that variations to the number of inlets and outlets may be made. For example, embodiments are envisaged with a sample inlet and no diluent buffer inlet. Further, embodiments may also comprise a single sample outlet or multiple sample outlets. The number of pumping modules and sample collection valves will vary according to the number of inlets and outlets on the microfluidic chip.

Figure 4:
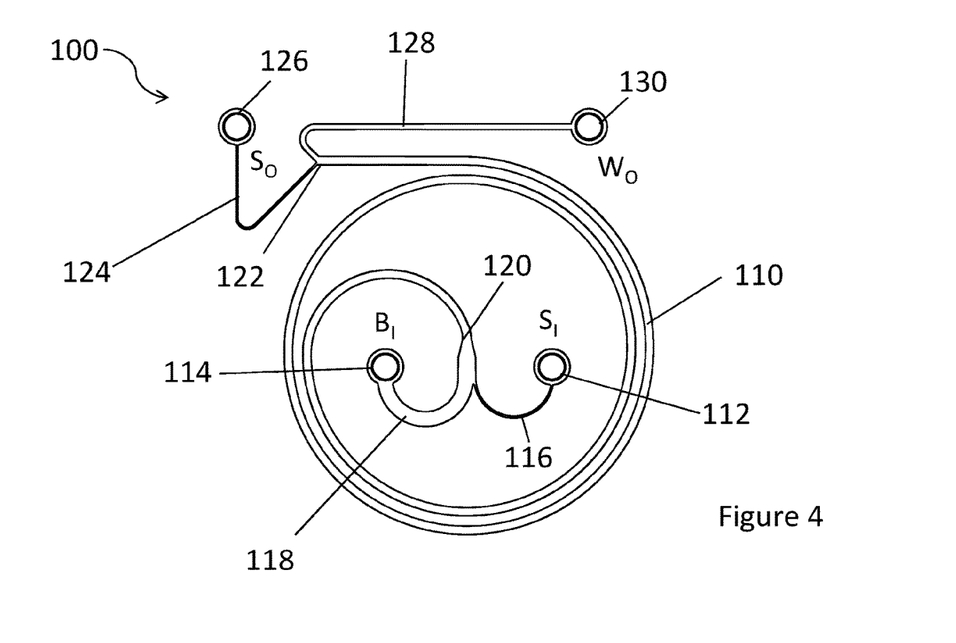
FIG. 4 shows an example of a microfluidic chip which may be used with embodiments of the present invention.

FIG. 4 shows an example of a microfluidic chip which may be used with embodiments of the present invention. It is noted that the microfluidic chip shown in FIG. 4 has one sample inlet, one diluent buffer inlet, one sample outlet and one waste outlet.

FIG. 4 shows a schematic of a biochip design described in international patent application PCT/SG2013/000442 (published as WO2015/057159) which may be used with embodiments of the present invention. The microfluidic device 100 comprises a spiral curved microchannel 110. A sample inlet $S_I$ 112 and a diluent buffer inlet $B_I$ 114 are located in a central region of the spiral curved microchannel 110. A sample inlet coupling path 116 couples the sample inlet to the spiral curved microchannel 110. A buffer inlet coupling path 118 couples the diluent buffer inlet 114 to the spiral curved microchannel 110. The sample inlet coupling path 116 and the diluent buffer inlet coupling path 118 join at a confluence 120 at an upstream end of the spiral curved microchannel 110. At the downstream end of the spiral curved microchannel 110 there is a bifurcation 120 where the channel splits into a sample outlet coupling path 124 and a waste outlet coupling path. The sample outlet coupling path 124 is connected to a sample outlet $S_O$ 126 and the waste outlet coupling path 128 is connected to a waste outlet $W_O$ 130. The samples are introduced into the spiral curved microchannel 110 from the outer side of the channel curvature. The cells will align to the outer channel wall with the help of diluent buffer. The curved spiral microchannel 110 is configured to separate large cells such as CTCs from smaller cells such as WBCs and RBCs. The dimensions of the curved spiral microchannel 110 are selected so that the smaller cells migrate across the channel under the influence of Dean forces, whereas the large cells are caused to focus and occupy a single equilibrium position. This means that after half of the Dean cycle both large and small cells will occupy the inner side of the channel. The length to the end of the curved section is selected so that the smaller cells will have completed one Dean cycle. Thus, at the end of the curved section, the smaller cells have finished one Dean cycle and will have migrated to the outer side of the channel. Therefore at the bifurcation 122, the larger CTCs are focussed at the inner channel wall and are collected from the sample outlet 126 whereas the smaller cells are in a separate stream at the outer channel wall and exit from the waste outlet 130.

Figure 5:
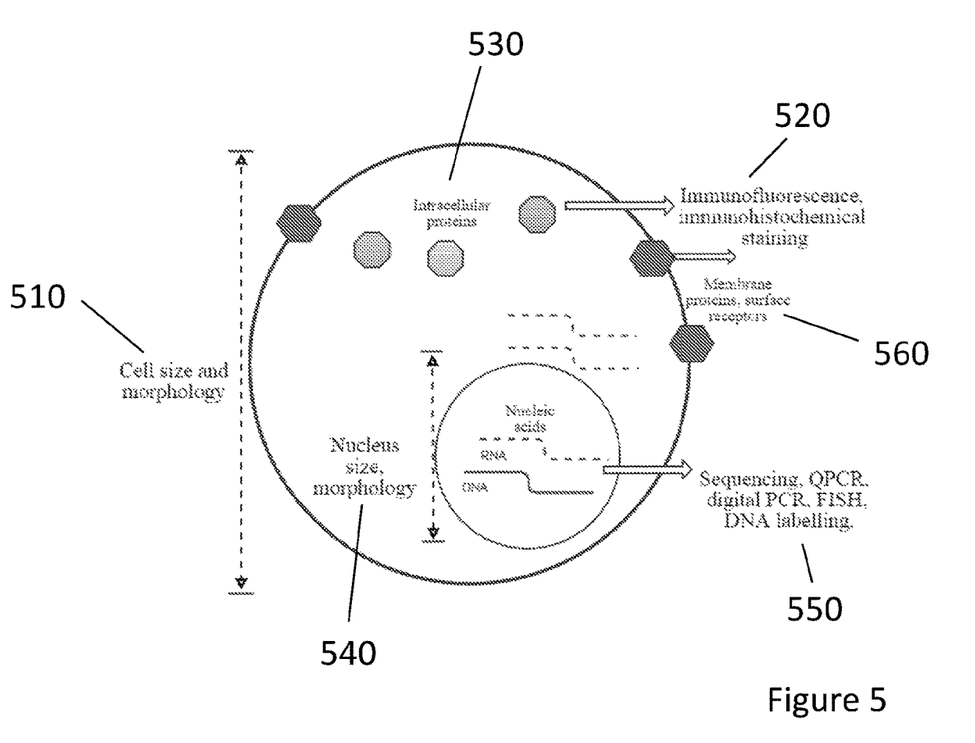
FIG. 5 illustrates the factors that may be used in the downstream analysis of the target cells.

FIG. 5 illustrates the factors that may be used in the downstream analysis of the target cells. The target cells may be cancer cells such as CTCs. Cancer cells typically display differential size and morphology from normal cells. Therefore one factor used in the downstream analysis is the cell size and morphology 510. Genetic aberrations, including somatic single nucleotide mutations, structural variants and chromatic fusions are evident in cancer cells. Gene and protein expression profiles of cancer cells are also different from other cell types, depending on its tissue origins and malignancy. Based on these distinct features of cancer cells, downstream analysis of the cells collected in the sample output container(s) can be performed to identify the cancer cells and its molecular profile.

As shown in FIG. 5, immuno-staining 520 of protein markers either intracellular 530 or on membrane surfaces 560 can be performed to visually evaluate a specific targeted protein expression to identify the cell type or features. Nuclear staining can be performed by nucleic acid fluorescence labelling and visually observed. Molecular characterization of the nucleic acids can be done by sequencing of the nucleic acids by next-generation sequencing (NGS) or Sanger sequencing, digital polymerase chain reaction (PCR), droplet digital PCR, quantitative PCR (qPCR) and fluorescence in-situ hybridization (FISH); the copy number of the nucleic acids of interest can be also be inferred by these methods. Morphological analysis of circulating tumour cells can be performed based on its size and shape of the cell 510 and its nucleus 540.

Figure 6:
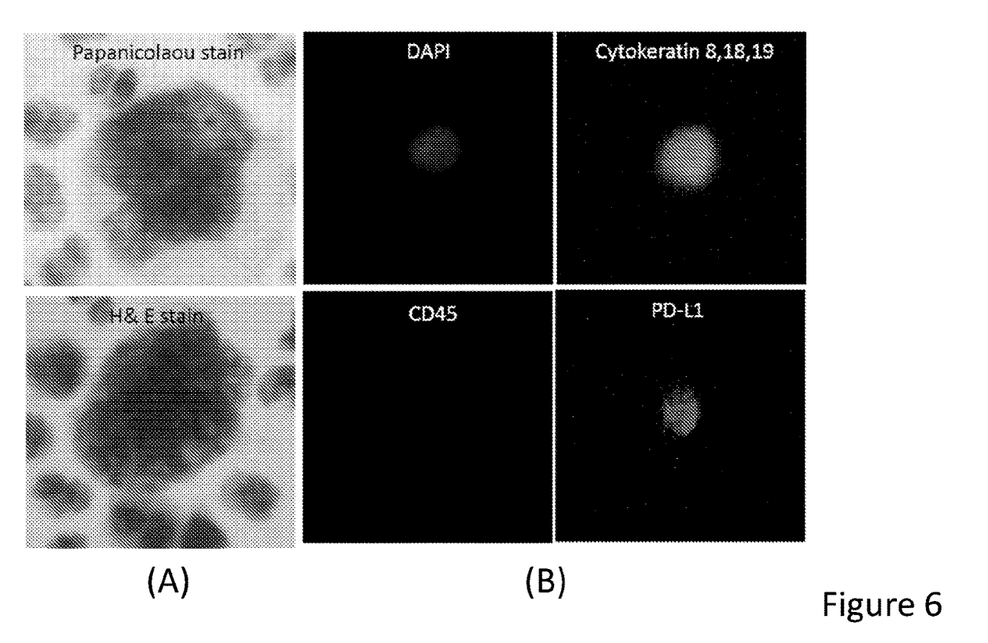
FIGS. 6A and 6B show identification of malignant tumour cells with morphological based and immunocytochemistry approaches.

FIGS. 6A and 6B show identification of malignant tumour cells with morphological based and immunocytochemistry approaches. FIG. 6A shows a morphological based approach, such as papanicolaou staining, Hematoxylin and Eosin (H&E), and Geimsa staining which enhance the contrast of the cells against the background, allowing direct visualization and identification of the malignant cells.

FIG. 6B shows examples of the use of immunocytochemistry, such as the use of using CD45 antibody as a negative marker, and antibodies cocktail for positive identification of tumour cells (Cytokeratin 8, 18, 19, EpCAM, CD133, TTF-1, Napsin, EGFR, etc). In FIG. 6B, a circulating tumor cell is labelled positive for nucleic acid marker—DAPI, epithelial markers—Cytokeratin 8, 18, 19 and immune checkpoint evasion marker—PD-L1, while negative for lymphocyte marker—CD45.

Figure 7:
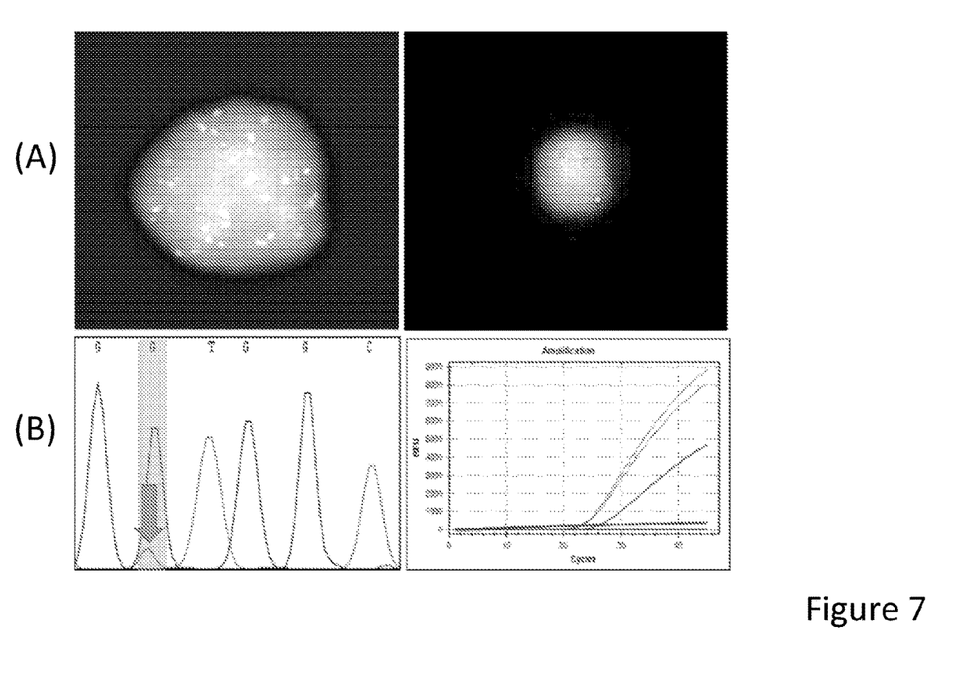
FIGS. 7A and 7B show the characterization of tumour cells with molecular based approaches, such as FISH and PCR based approaches.

FIGS. 7A and 7B show the characterization of tumour cells with molecular based approaches, such as FISH and PCR based approaches respectively.

As shown in FIG. 7A, FISH detection of chromosomal aberration could be performed to identify tumour cells which often present genetic aberrations, such as chromosomal amplification, polyploidy, aneuploidy (left) and gene fusion (right).

FIG. 7B shows the detection of point mutation. The left panel shows detection of a point mutation (peak indicated by arrow) in the KRAS oncogene using Sanger sequencing of tumour cells. The right panel shows fluorescent detection of EGFR L858R mutation using an allele-specific based qPCR assay.

Figure 8:
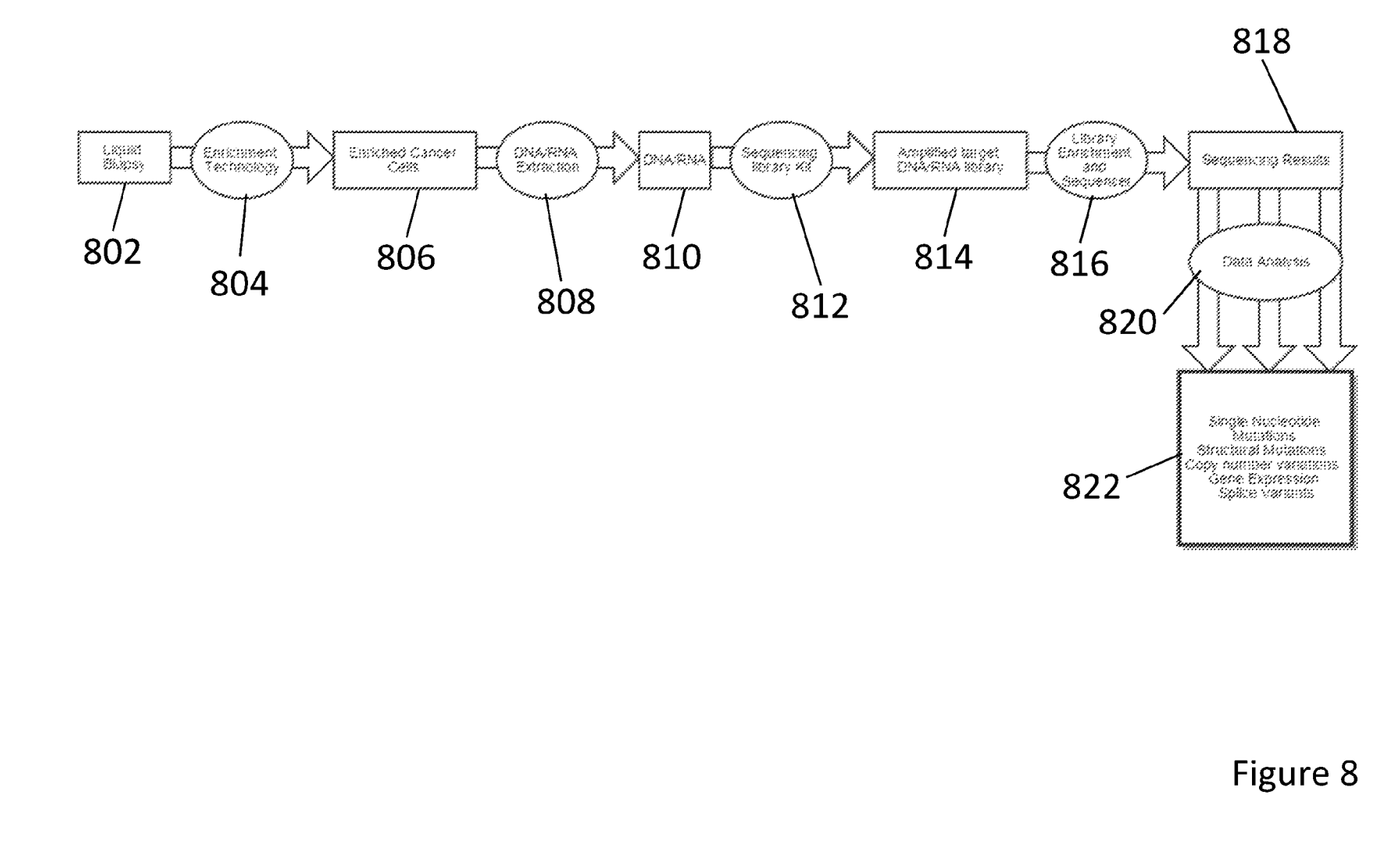
FIG. 8 shows an example of processing cancer cells that are enriched from liquid biopsy can be processed for next-generation sequencing.

FIG. 8 shows an example of processing cancer cells that are enriched from liquid biopsy can be processed for next-generation sequencing. In step 802, a liquid biopsy is taken. In step 804, the cancer cells are enriched using an enrichment system as described herein. This provides enriched cancer cells 806. After cancer cell enrichment, nucleic acid extraction can be performed in step 808 to obtain pure DNA or RNA 810. Nucleic acid target regions can be amplified or enriched using appropriate sequencing library kits in step 812. This results in an amplified target DNA or RNA library 814. The sequencing library template can be further enriched and sequenced on appropriate sequencers in step 816. The sequencing results 818 are analysed in step 820 to discover for any genomic or transcriptomic patterns including mutations (single nucleotide or structural), copy number variations, gene expression and splice variants 822.

As described above, visual and molecular profiling may be interpreted to infer disease information, such as risk of metastasis, prognosis, therapeutic targets that steer personalized therapeutic decisions. For instance, chromosomal translocation of ALK detected by FISH, KRAS mutation detected by Sanger sequencing and qPCR detection of EGFR L858R provide therapeutic targets for specific antagonists. Next-generation sequencing of cancer cells enriched can be useful for detection of mutations, copy number changes, gene expression changes or RNA splice variants that could be relevant to cancer pathogenesis. In addition, molecular profiling of CTCs allows for research and better understanding into the evolution and mechanisms of metastasis and cancer progression for discovery of therapeutic strategies and novel biomarkers.

Figure 9:
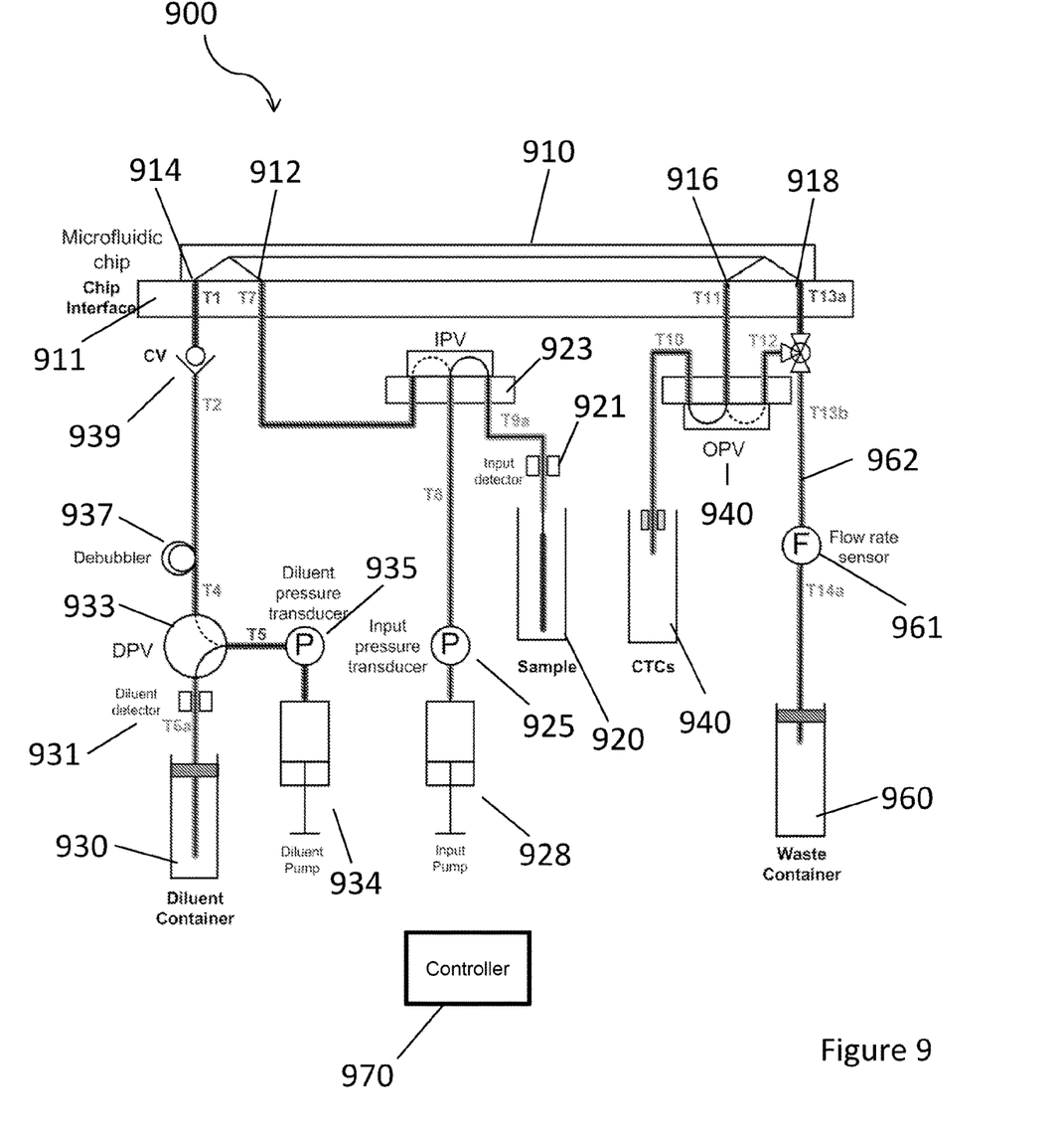
FIG. 9 shows a system for enriching target cells according to an embodiment of the present invention.

FIG. 9 shows a system for enriching target cells according to an embodiment of the present invention. The system 900 comprises a microfluidic chip 910. The microfluidic chip 910 may be of the form described above in relation to FIG. 4. The microfluidic chip 910 has a sample inlet 912, a diluent buffer inlet 914, a sample outlet 916 and a waste outlet 918. A chip interface 911 provides coupling with a leak-proof seal between the microfluidic chip 910 and tubes which are in fluid communication with the inlets and outlets of the microfluidic chip.

A sample container 920 contains the sample fluid which includes target cells to be enriched. A sample input pump 928 which in this embodiment is a syringe is coupled to the sample container 920 via an input pump switching valve IPV 923. The syringe may be mounted on a syringe pump that is controlled by a controller 970. The sample input pump 928 is configured to aspirate the input cells sample from an external container into the enrichment platform and pump through the microfluidic chip. The input pump switching valve IPV 923 is configured to switch between the input cell sample container 920 and the sample inlet 912 of the microfluidic chip 910. A tube T9a connects the sample container 920 with the input pump switching valve IPV 923. An input detector 921 is arranged on the tube T9a. The purpose of the input detector 921 is to prevent the loading of any air or air bubbles into the sample input pump 928. Air bubbles can be catastrophic to many microfluidic chip operation and affect separation quality by disrupting the fluid flow lines. Hence, it is important to ensure that no air enters the fluidic network.

A tube T8 connects the sample input pump 928 to the input pump switching valve IPV 923. An input pressure transducer 925 is located on the tube T8. The input pressure transducer 925 is a pressure transducer to measure the input pump pressure during pumping to ensure the sample input pump 928 is pumping at the desired rate. A tube T7 connects the input pump switching valve IPV 923 to the sample inlet 912 of the microfluidic chip 910.

A diluent container 930 contains the diluent buffer fluid. The diluent buffer comprises an isotonic solution to maintain high cell integrity during processing. The diluent buffer may also be supplemented with a surfactant solution to reduce the shear experienced by the cells and retain viability. Due to the small dimensions of the microfluidic chips, the shear rate within these chips can be very high and affect cell integrity (cells can be blown up) and viability (cell death). To minimize these shear effects, the diluent buffer and the input cell sample buffer contain surfactant that provides "cell-cushioning" effects and keeps the cells intact.

A diluent pump 934 which in this embodiment is a syringe is coupled to the diluent container 930 via a diluent pump switching valve DPV 933. The diluent pump 934 is configured to aspirate and pump the diluent buffer fluid from the diluent container 930 into the enrichment platform and pump through the microfluidic chip 910. The diluent pump switching valve DPV 933 is configured to switch between the diluent container 930 and the diluent inlet 914 of the microfluidic chip 910. A tube T6a connects the diluent container 930 with the diluent pump switching valve DPV 933. A diluent detector 931 is located on the tube T6a. The diluent detector 931 prevents the loading of any air or air bubbles into the diluent pump. Air bubbles can be catastrophic to many microfluidic chip operation and affect separation quality by disrupting the fluid flow lines. Hence, it is important to ensure that no air enters the fluidic network. The diluent detector 931 is a liquid detection sensor. If the diluent detector 931 detects no diluent flowing through the tube T6a (i.e. the sensor is activated), then the controller 970 sends a message to the user to refill/replace the diluent container 930 with diluent.

A tube T5 connects the diluent pump switching valve DPV 933 with the diluent pump 924. A diluent pressure transducer 935 is located on the tube T5. The diluent pressure transducer 935 is a pressure transducer to measure the diluent buffer pressure during pumping to ensure the diluent pump 924 is pumping at the desired rate.

A tube T4 connects the diluent pump switching valve DPV 933 to a debubbler 933. A tube T2 connects the debubbler 933 to a check valve CV 939. A tube T1 connects the check valve CV 939 to the diluent inlet 914 of the microfluidic chip 910. The diluent detector 931 has a threshold limit above which it can detect air bubbles and trigger an alert. However, smaller bubbles may still pass through without activating the diluent detector 931. These bubbles can then be removed by a debubbler 933 which may comprise an air permeable membrane letting air escape, thus removing air bubbles. In another embodiment, the debubbler 931 may comprise a vacuum pump to suck out air bubbles from the diluent buffer.

The sample outlet 916 of the microfluidic chip 910 is connected to an output switching valve OPV 942 by a tube T11. The output switching valve OPV 942 is configured to switch the output of the sample outlet 916 between a CTC sample collection container 940 and a waste container 960. A tube T10 connects one output of the output switching valve OPV 942 to the CTC sample collection container 940. A tube T12 connects to the other output of the output switching valve OPV 942 and forms part of a waste output branch 962. The waste output branch 962 further comprises a tube T13a which connects to the waste outlet 918 of the microfluidic chip 910. A tube T13b connects the tube T12 which runs from the output switching valve OPV 942 and the tube T13a which runs from the waste outlet 918 of the microfluidic chip 910 with a flow rate sensor 961. A further tube T14a runs from the flow rate sensor 961 to the waste container 960.

The flow rate sensor 961 monitors the flow rate at the output side to ensure that the flow ratio between T11 and T13a can be polled during the separation phase. The flow rate ratio between the target cells output and the waste output for a two output biochip, for example, can hence been used as a parameter to assess the quality of enrichment. If this ratio is lower than the set value, then the recovery of the target cells (malignant tumour cells) may decrease as more cells are lost to the waste. On the contrary, if the said ratio is higher than the set value, there will be more contaminating non-target cells that would be collected with the target cells thus decreasing enrichment. This ratio may vary considerably during manual manipulation as the output tubing resistance, and open pressure may not be well controlled.

A controller 970 monitors the output of the flow rate sensor 961 and controls the output switching valve OPV 942. Thus, the output switching valve OPV 942 provides switching of the sample outlet 916 of the microfluidic chip 910 between the CTC sample container 940 and the waste container 960. The output switching valve OPV 942 along with the flow rate sensor 961 helps to achieve reliable enrichment. For example, if the flow ratio between T11 and T13a goes out of desired range, this valve can switch and direct all the output from T11 to the waste, thereby not compromising the quality of the enriched CTC sample. Once the flow ratio returns within the desired range, the OPV can switch back and collect the enriched target (CTCs) cells in the CTC container.

When a new input cell sample is loaded on this automated enrichment platform the controller 970 may control the process as follows. The user can select a desired run protocol based on the input sample and the microfluidic chip. Once started, controller 970 will control the diluent pump switching valve DPV 933 will switch to the diluent buffer container 930 and the diluent pump 934 will aspirate the diluent buffer required to process this sample. Similarly, the controller 970 will control the input pump switching valve IPV 923 to switch and the input pump 928 will aspirate the input cell sample from the input container 920. Once the two pumps have aspirated appropriate amounts of diluent buffer and sample, the diluent pump switching valve DPV 933 and input pump switching valve IPV 923 will be controlled by the controller 970 to switch and connect the pumps to the microfluidic chip 910 via the chip interface 911.

As the sample and diluent buffer flow through the microfluidic chip 910, the target cells (CTCs) are separated from the remaining cells using inertial forces and Dean flows. The target cells are then directed to the sample outlet 916 and the tube T11 and collected in the CTC sample container 940, while the non-target cells are collected in the waste container 960 via the waste output branch 962. The flow rate sensor 961 monitors the flow rate throughout the entire separation process to ensure a pre-determined flow ratio is achieved. As the total flow rate through the microfluidic chip 910 is controlled by the controller 970 which controls the input pump 928 and the diluent pump 934, by measuring the flow rate through the waste output branch, we can calculate the flow ratio. If at any instance a deviation from the pre-determined flow ratio is detected, the controller 970 causes the output switching valve OPV 942 to switch its output to the waste output branch 962 ensuring no output is collected in the CTC sample container 940 during the flow fluctuation period. Once the flow in the microfluidic chip re-stabilizes, the output switching valve OPV 942 is controlled by the controller 970 to switch back and the output from the sample outlet 916 of the microfluidic chip 910 to the CTC sample container 940. A large flow fluctuation outside the acceptable range can affect the separation quality. The range of flow rate fluctuation acceptable can be a percentage of the flow rate measured at 961, for example 5% or 10%.

In an embodiment, the system comprises a second flow rate sensor arranged on the tube T11 connecting the sample outlet 916 of the microfluidic chip 910 to the output switching valve OPV 942.

Those of skill in the art will appreciate that various modifications and changes in form and details may be made to the embodiments described herein without departing from the scope of the invention defined by the appended claims.

The invention claimed is:

1. A system for enriching target cells in a sample, the system comprising:
a microfluidic chip comprising a sample inlet, a sample outlet, a waste outlet and a microfluidic channel, the sample inlet being coupled to an upstream end of the microfluidic channel and the sample outlet and the waste outlet being coupled to a downstream end of the microfluidic channel, the microfluidic chip being configured such that target cells are directed to the sample outlet and non-target cells are directed to the waste outlet;
a sample input pump configured to introduce the sample into the sample inlet of the microfluidic chip;
a first output flow rate detector configured to measure a flow rate at the sample outlet or the waste outlet of the microfluidic chip;
a sample collection switching valve having a configuration switchable between a first configuration in which the sample output of the microfluidic chip is coupled to a sample output container and a second configuration in which the sample output of the microfluidic chip is coupled to a waste output container; and a controller configured to control the configuration of the sample collection switching valve using the flow rate measured by the first output flow rate detector, wherein the controller is configured to determine a flow ratio between the sample outlet and the waste outlet and further configured to compare the flow ratio with a predetermined range of flow ratios and to switch the sample collection switching valve to the second configuration if the flow ratio is outside the predetermined range of flow ratios, the predetermined range of flow ratio being fixed by controlling resistance of tubing of the sample outlet and the waste outlet.

2. The system of claim 1, wherein the controller is configured to compare the flow rate measured by the first output flow rate detector with a predetermined range of flow rate values, and the controller is further configured to switch the sample collection switching valve to the second configuration if the flow rate measured by the first output flow rate detector is outside the predetermined range of flow rate values.

3. The system of claim 1, wherein the controller is configured to determine the flow ratio from the flow rate measured by the first output flow rate detector and a total flow rate through the microfluidic chip.

4. The system of claim 1, wherein the first output flow rate detector is configured to measure a flow rate at the waste outlet, the system further comprises a second output flow rate detector configured to measure a flow rate at the sample outlet of the microfluidic chip, wherein the controller is configured to determine the flow ratio from the flow rate measured at the waste outlet by the first flow rate detector and the flow rate measured at the sample outlet by the second flow rate detector.

5. The system of claim 1, wherein the sample comprises a density matching liquid having a density selected such that the target cells are uniformly suspended in the sample during processing.

6. The system of claim 1, wherein the microfluidic chip further comprises a diluent inlet coupled to the upstream end of the microfluidic channel and the system further comprise a diluent inlet pump configured to introduce a diluent buffer into the diluent inlet.

7. The system of claim 6, further comprising a debubbler arranged to remove bubbles from the diluent buffer.

8. The system of claim 1, wherein the target cells are circulating tumour cells.

9. The system of claim 1, wherein the microfluidic channel comprises a spiral or curved section.

10. A method of enriching target cells in a sample, using a microfluidic chip, the microfluidic chip comprising a sample inlet, a sample outlet, a waste outlet and a microfluidic channel, the sample inlet being coupled to an upstream end of the microfluidic channel and the sample outlet and the waste outlet being coupled to a downstream end of the microfluidic channel, the microfluidic chip being configured such that target cells are directed to the sample outlet and non-target cells are directed to the waste outlet; the method comprising:

introducing the sample into the sample inlet of the microfluidic chip;

monitoring a flow rate at the sample outlet or the waste outlet of the microfluidic chip;

controlling the configuration of a sample collection switching valve using the monitored flow rate, the sample collection switching valve having a configuration switchable between a first configuration in which the sample output of the microfluidic chip is coupled to a sample output container and a second configuration in which the sample output of the microfluidic chip is coupled to a waste output container; and determining a flow ratio between the sample outlet and the waste outlet, comparing the flow ratio with a predetermined range of flow ratios and to switching the sample collection switching valve to the second configuration if the flow ratio is outside the predetermined range of flow ratios, the predetermined range of flow ratio being fixed by controlling resistance of tubing of the sample outlet and the waste outlet.

11. The method of claim 10, further comprising suspending the sample in a density matching liquid prior to introducing the sample into the sample inlet of the microfluidic chip, the density matching liquid having a density selected such that the target cells are uniformly suspended in the sample during processing.

12. The method of claim 10, further comprising performing centrifugation and or blood lysis on the sample before introducing the sample into the sample inlet of the microfluidic chip.

13. The method of claim 10, further comprising comparing the monitored flow rate with a predetermined range of flow rate values, and switching the sample collection switching valve to the second configuration if the monitored flow rate is outside the predetermined range of flow rate values.

14. The method of claim 10, wherein determining the flow ratio comprises determining the flow ratio from the monitored flow rate and a total flow rate through the microfluidic chip.

15. The method of claim 10, wherein the monitored flow rate is the flow rate at the waste outlet of the microfluidic chip, the method further comprises measuring a flow rate at the sample outlet, wherein determining the flow ratio comprises determining the flow ratio from the monitored flow rate and the measured flow rate at the sample outlet.

16. The method of claim 10, wherein the microfluidic chip further comprises a diluent inlet coupled to the upstream end of the microfluidic channel and the method further comprises introducing a diluent buffer into the diluent inlet.

17. The method of claim 16, further comprising removing bubbles from the diluent buffer before introducing the diluent buffer into the diluent inlet.

18. The method of claim 10, wherein the target cells are circulating tumour cells.

19. The method of claim 10, wherein the microfluidic channel comprises a spiral or curved section.

20. A method of analysing a sample, the method comprising:

enriching target cells in the sample using a method of claim 10; and analysing the enriched target cells for diagnostic use.

* * * * *